United States Patent
Kim et al.

(10) Patent No.: US 9,921,051 B2
(45) Date of Patent: Mar. 20, 2018

(54) THICKNESS MEASURING APPARATUS AND THICKNESS MEASURING METHOD

(71) Applicant: KOREA RESEARCH INSTITUTE OF STANDARDS AND SCIENCE, Daejeon (KR)

(72) Inventors: Jae-Wan Kim, Daejeon (KR); Jong-Ahn Kim, Daejeon (KR); Chu-Shik Kang, Daejeon (KR); Jong-Han Jin, Daejeon (KR)

(73) Assignee: Korea Research Institute of Standards and Science, Daejeon (KR)

( * ) Notice: Subject to any disclaimer, the term of this patent is extended or adjusted under 35 U.S.C. 154(b) by 810 days.

(21) Appl. No.: 14/323,211

(22) Filed: Jul. 3, 2014

(65) Prior Publication Data
US 2015/0012246 A1 Jan. 8, 2015

(30) Foreign Application Priority Data
Jul. 5, 2013 (KR) .......................... 10-2013-0078751

(51) Int. Cl.
*G01B 11/06* (2006.01)
*G01B 11/14* (2006.01)
(Continued)

(52) U.S. Cl.
CPC ............ *G01B 11/06* (2013.01); *G01B 9/0201* (2013.01); *G01B 9/02081* (2013.01);
(Continued)

(58) Field of Classification Search
None
See application file for complete search history.

(56) References Cited

U.S. PATENT DOCUMENTS 5,631,736 A * 5/1997 Thiel ................. G01B 9/02004
356/486
8,625,111 B2 1/2014 Sai et al.
(Continued)

FOREIGN PATENT DOCUMENTS

JP 4861281 B2 1/2012
KR 10-1317536 B1 10/2013

OTHER PUBLICATIONS

Yang et al., "Research on full field test of film thickness by dual wavelength laser interference," School of Optoelectronic Engineering, Xi'an Technological University, Xi'an 710032, China, vol. 38, pp. 282-286, dated Nov. 2009.
(Continued)

*Primary Examiner* — Gregory J Toatley
*Assistant Examiner* — Terence Stifter, Jr.
(74) *Attorney, Agent, or Firm* — Jenkins, Wilson, Taylor & Hunt, P.A.

(57) ABSTRACT

Provided are a thickness measuring apparatus and a thickness measuring method. The thickness measuring method includes irradiating a first laser beam of a first wavelength $\lambda_1$ to a transparent substrate and measuring intensity of the first laser beam transmitting through the transparent substrate; irradiating a second laser beam of a second wavelength $\lambda_2$ to the transparent substrate and measuring intensity of the second laser beam transmitting through the transparent substrate; and extracting a rotation angle on a Lissajous graph using the first and second laser beams transmitting through the transparent substrate. A phase difference between adjacent rays by multiple internal reflection of the first laser beam and a phase difference between adjacent rays by multiple internal reflection of the second laser beam is maintained at $\pi/2$.

21 Claims, 13 Drawing Sheets

(51) Int. Cl.
  *G01B 9/02* (2006.01)
  *G01N 21/21* (2006.01)
  *G01S 17/36* (2006.01)
  *G01N 21/45* (2006.01)

(52) U.S. Cl.
  CPC ............ *G01B 11/14* (2013.01); *G01N 21/211* (2013.01); *G01N 21/45* (2013.01); *G01N 2021/213* (2013.01); *G01S 17/36* (2013.01)

(56) References Cited

U.S. PATENT DOCUMENTS

| | | | | |
|---|---|---|---|---|
| 2005/0018183 A1* | 1/2005 | Shortt | ................ | G01B 11/0633 356/239.1 |
| 2005/0248773 A1* | 11/2005 | Rosencwaig | ...... | G01B 11/0625 356/504 |
| 2007/0024860 A1* | 2/2007 | Tobiason | ........... | G01B 9/02004 356/498 |
| 2007/0195328 A1* | 8/2007 | Tan | .......................... | G01J 3/26 356/454 |
| 2008/0180679 A1* | 7/2008 | de Groot | ............ | G01B 9/02004 356/450 |
| 2009/0213386 A1* | 8/2009 | LeBlanc | ............ | G01B 11/2441 356/495 |

OTHER PUBLICATIONS

Chinese Office Action for Chinese Application No. 201410320417.6 dated Sep. 30, 2017.

\* cited by examiner

THICKNESS MEASURING APPARATUS AND THICKNESS MEASURING METHOD

CROSS-REFERENCE TO RELATED APPLICATION

This U.S. non-provisional application claims priority under 35 U.S.C. § 119 to Korea Patent Application No. 10-2013-0078751 filed on Jul. 5, 2013, the entirety of which is hereby incorporated by reference herein.

BACKGROUND

Field of the Invention

The present invention relates to thickness measuring apparatuses and thickness measuring methods. More specifically, the present invention is directed to thickness measuring apparatuses and thickness measuring methods capable of precisely measuring variation of thickness using two wavelengths.

Description of the Related Art

Substrates of glass or the like are used in semiconductor devices or flat panel displays such as liquid crystal display (LCD) and organic light emitting diode (OLED). In recent years, display devices are trending toward large-area and high-resolution display devices. Accordingly, substrates included in display devices continue to grow in area. Since non-uniform thickness of such a substrate may have an adverse effect on the resolution of a display device, it is necessary to keep thickness uniform on the entire surface of the substrate.

In general, a reflection-type thickness measuring apparatus using interference between lights reflected from front and back surfaces of a substrate is used to measure thickness variation of a few nanometers (nm) to tens of nanometers (nm). However, as an area of a substrate grows, the substrate may be warped while measuring thickness of the substrate. As the substrate is warped, a path of light reflected from the substrate is changed to make it difficult to precisely measure thickness of the substrate.

SUMMARY

Embodiments of the present invention provide a thickness measuring apparatus and a thickness measuring method for measuring thickness of a thin film using two wavelengths which satisfy a predetermined condition.

A thickness measuring method according to an embodiment of the present invention may include irradiating a first laser beam of a first wavelength $\lambda_1$ to a transparent substrate and measuring the intensity of the first laser beam transmitted through the transparent substrate; irradiating a second laser beam of a second wavelength $\lambda_2$ to the transparent substrate and measuring the intensity of the second laser beam transmitted through the transparent substrate; and extracting a rotation angle on a Lissajous graph using the first and second laser beams transmitting through the transparent substrate. A phase difference between adjacent rays by multiple internal reflection of the first laser beam and a phase difference between adjacent rays by multiple internal reflection of the second laser beam may be maintained at $\pi/2$.

In an exemplary embodiment of the present invention, the thickness measuring method may further include transferring the transparent substrate.

In an exemplary embodiment of the present invention, the thickness measuring method may further include removing a nonlinearity error from the rotation angle.

In an exemplary embodiment of the present invention, the transmitted first and second laser beams $I_x$ and $I_y$ are expressed as below:

$$I_x = A_x + B_x \cos\left(\phi + \frac{\delta}{2}\right)$$
$$I_y = A_y + B_y \sin\left(\phi - \frac{\delta}{2}\right)$$

wherein $A_x$ and $A_y$ represent DC offsets, $B_x$ and $B_y$ represent AC amplitudes, $\delta$ represents a phase difference indicating the degree of getting out of 90 degrees, and $\varphi$ represents a phase difference proportional to thickness of the transparent substrate, and wherein the parameters $A_x$, $B_x$, $A_y$, $B_y$, and $\delta$ are updated under a condition in which the rotation angle becomes an integer multiple of $\pi/4$.

A thickness measuring method according to another embodiment of the present invention may include measuring intensity of a first transmitted beam of a first wavelength transmitting at a first position of a transparent substrate; expanding an Airy function using Taylor series expansion under a condition in which a coefficient of finesse is smaller than 1 such that the first transmitted beam of the first wavelength transmitting through the transparent substrate given as an Airy function is displayed as a cosine function to a phase difference caused by optical path length between adjacent rays transmitted through multiple internal reflection of the transparent substrate; selecting a second wavelength to transform the cosine function into a sine function; measuring intensity of a second transmitted beam of the second wavelength transmitting at the first position of the transparent substrate; processing the intensity of the first transmitted beam and the intensity of the second transmitted beam to extract a rotation angle on a Lissajous graph; and calculating the thickness of the transparent substrate using the rotation angle.

In an exemplary embodiment of the present invention, the thickness measuring method may further include changing a measurement position of the transparent substrate.

In an exemplary embodiment of the present invention, the thickness measuring method may further include removing a nonlinearity error from the rotation angle.

A thickness measuring method according to another embodiment of the present invention may include preparing a first measurement signal of first transmitted beam of a first wavelength transmitting at a first position of a transparent substrate; expanding an Airy function using Taylor series expansion under a condition in which the first transmitted beam of the first wavelength transmitting through the transparent substrate is given as an Airy function and a coefficient of finesse is smaller than 1 such that the first transmitted beam is displayed as a cosine function to a phase difference caused by optical path length between adjacent rays transmitted through multiple internal reflection of the transparent substrate; selecting a second wavelength to transform the cosine function into a sine function; preparing a second measurement signal of a second transmitted beam of a second wavelength transmitting at the first position of the transparent substrate; processing the first measurement signal and the second measurement signal to extract a rotation angle on a Lissajous graph; and calculating thickness of the transparent substrate using the rotation angle.

A thickness measuring method according to another embodiment of the present invention may include preparing a first measurement signal of first transmitted beam of a first wavelength $\lambda_1$ transmitting a first position of a transparent substrate; preparing a second measurement signal of a second transmitted beam of a second wavelength $\lambda_2$ transmitting at the first position of the transparent substrate; processing the first measurement signal and the second measurement signal to extract a rotation angle on a Lissajous graph; and calculating thickness of the transparent substrate using the rotation angle. The first wavelength and the second wavelength may satisfy a condition below:

$$\frac{4\pi}{\lambda_2} nd\cos(\theta_2) = \frac{4\pi}{\lambda_1} nd\cos(\theta_2) - \frac{\pi}{2}$$

$$\lambda_2 = \lambda_1 + \Delta\lambda$$

$$\Delta\lambda \approx \frac{\lambda_1^2}{8nd\cos(\theta_2)}$$

wherein n represents a refractive index, d represents average thickness of the transparent substrate 10, and $\theta_2$ represents a refraction angle.

A thickness measuring apparatus according to an embodiment of the present invention may include a first laser outputting a laser beam of a first wavelength; a second laser outputting a laser beam of a second wavelength; an optical coupler coupling an output of the first laser and an output of the second laser with each other and providing the combined output to a first position of a transparent substrate; a dichromatic beam splitter splitting the first transmitted beam of the first wavelength and the second transmitted beam of the second wavelength from each other; a first optical detector measuring the first transmitted beam of the first wavelength split through the dichromatic beam splitter; a second optical detector measuring the second transmitted beam of the second wavelength split through the dichromatic beam splitter; and a processing unit extracting a rotation angle on a Lissajous graph using intensity of the first transmitted beam of the first wavelength and intensity of the second transmitted beam of the second wavelength, a difference in optical path length between adjacent rays caused by internal reflection of the transparent substrate at the first position, or a phase difference between adjacent rays caused by the internal reflection of the transparent substrate at the first position.

In an exemplary embodiment of the present invention, the intensity of the first transmitted beam of the first wavelength may have a cosine function according to the phase difference, and the intensity of the second transmitted beam of the second wavelength may have a sine function according to the phase difference.

In an exemplary embodiment of the present invention, the optical coupler may include a beam splitter transmitting the laser beam of the first wavelength and reflecting the laser beam of the second wavelength; and a reflection mirror reflecting the laser beam of the second wavelength and providing the reflected laser beam to the beam splitter.

In an exemplary embodiment of the present invention, the thickness measuring apparatus may further include a transfer unit transferring the transparent substrate; and a transfer driving unit driving the transfer unit.

A thickness measuring apparatus according to another embodiment of the present invention may include a first laser outputting a first pulse beam having a first wavelength and a first period; a second laser outputting a second pulse beam oscillating at different time from the first pulse beam and having a second wavelength and the first period; an optical coupler providing an output of the first laser or an output of the second laser to a first position of a transparent substrate; an optical detector sequentially measuring a first transmitted beam of the first wavelength and second transmitted beams of the second wavelength transmitting through the transparent substrate; and a processing unit extracting a rotation angle on a Lissajous graph using intensity of the first transmitted beam of the first wavelength and intensity of the second transmitted beam of the second wavelength, a difference in optical path length between adjacent rays caused by internal reflection of the transparent substrate at the first position, or a phase difference between adjacent rays caused by the internal reflection of the transparent substrate at the first position.

In an exemplary embodiment of the present invention, the intensity of the first transmitted beam of the first wavelength may have a cosine function according to the phase difference, and the intensity of the second transmitted beam of the second wavelength may have a sine function according to the phase difference.

In an exemplary embodiment of the present invention, the optical coupler may include a beam splitter transmitting the first pulse beam of the first wavelength and reflecting the second pulse beam of the second wavelength; and a reflection mirror reflecting the second pulse beam of the second wavelength and providing the reflected second pulse beam to the beam splitter.

In an exemplary embodiment of the present invention, the thickness measuring apparatus may further include a transfer unit transferring the transparent substrate; and a transfer driving unit driving the transfer unit.

A thickness measuring apparatus according to another embodiment of the present invention may include a first laser outputting a laser beam of a first wavelength; a second laser outputting a laser beam of a second wavelength; an optical switch receiving an output of the first laser and an output of the second laser and periodically and alternately providing the first laser beam and the second laser beam to a first position of a transparent substrate; an optical detector measuring a first transmitted beam of the first wavelength or second transmitted beams of the second wavelength transmitting through the transparent substrate; and a processing unit extracting a rotation angle on a Lissajous graph using intensity of the first transmitted beam of the first wavelength and intensity of the second transmitted beam of the second wavelength, a difference in optical path length between adjacent rays caused by internal reflection of the transparent substrate at the first position, or a phase difference between adjacent rays caused by the internal reflection of the transparent substrate at the first position.

In an exemplary embodiment of the present invention, the intensity of the first transmitted beam of the first wavelength may have a cosine function according to the phase difference, and the intensity of the second transmitted beam of the second wavelength may have a sine function according to the phase difference.

In an exemplary embodiment of the present invention, the thickness measuring apparatus may further include a transfer unit transferring the transparent substrate; and a transfer driving unit driving the transfer unit.

A thickness measuring apparatus according to another embodiment of the present invention may include a first laser outputting a first laser beam of a first wavelength; a second laser outputting a second laser beam of a second wavelength; a wavelength-division multiplexer receiving and multiplexing the first laser beam and the second laser beam into a single output and providing the single output to a first position of a transparent substrate; an optical detector measuring a first transmitted beam of the first wavelength or second transmitted beams of the second wavelength transmitting through the transparent substrate; and a processing unit extracting a rotation angle on a Lissajous graph using intensity of the first transmitted beam of the first wavelength and intensity of the second transmitted beam of the second wavelength, a difference in optical path length between adjacent rays caused by internal reflection of the transparent substrate at the first position, or a phase difference between adjacent rays caused by the internal reflection of the transparent substrate at the first position.

In an exemplary embodiment of the present invention, the thickness measuring apparatus may further include a wavelength-division demultiplexer receiving the first transmitted beam and the second transmitted beam through a single input port, outputting the first transmitted beam of the first wavelength to a first output port, and outputting the second transmitted beam of the second wavelength to a second output port. The optical detector may include a first optical detector connected to the first output port of the wavelength-division demultiplexer; and a second optical detector connected to the second output port of the wavelength-division demultiplexer.

In an exemplary embodiment of the present invention, the first laser beam of the first laser and the second laser beam of the second laser may be in form of a periodical pulse, and the first laser beam and the second laser beam may not temporally overlap each other.

A thickness measuring apparatus according to another embodiment of the present invention may include a first laser outputting a first laser beam of a first wavelength; a second laser outputting a second laser beam of a second wavelength; an optical coupler receiving and outputting the first laser beam and the second beam to a single path; a pattern beam generator disposed between the optical coupler and a transparent substrate to generate pattern beam; an optical detector array measuring the first transmitted beam of the first wavelength and the second transmitted beam of the second wavelength transmitting through the transparent substrate; and a processing unit extracting a rotation angle on a Lissajous graph using intensity of the first transmitted beam of the first wavelength and intensity of the second transmitted beam of the second wavelength, a difference in optical path length between adjacent rays caused by internal reflection of the transparent substrate at the first position, or a phase difference between adjacent rays caused by the internal reflection of the transparent substrate at the first position.

In an exemplary embodiment of the present invention, the pattern beam generator may include a diffraction grating element diffracting received beam to generate a plurality of beams aligned in a constant direction; and a collimation lens converting a ray transmitting through the diffraction grating element to parallel rays.

BRIEF DESCRIPTION OF THE DRAWINGS

The present invention will become more apparent in view of the attached drawings and accompanying detailed description. The embodiments depicted therein are provided by way of example, not by way of limitation, wherein like reference numerals refer to the same or similar elements. The drawings are not necessarily to scale, emphasis instead being placed upon illustrating aspects of the present invention.

DETAILED DESCRIPTION

When coherent light impinges on a transparent substrate, a transmitted beam transmitting through the substrate through multiple internal reflection may generate an interfering signal. The interfering signal of the transmitted beam may be dependent on the difference in optical path length or the difference in phase between adjacent rays by internal reflection. When thickness of the transparent substrate varies, the differencein optical path length or the difference in phase between adjacent rays by internal reflection may also vary. The interfering signal of the transmitted beam may have an Airy function. The Airy function may have $2\pi$ ambiguity depending on the phase difference. Thus, the interfering signal of the transmitted beam cannot specify the thickness of the transparent substrate.

According to an embodiment of the present invention, a trajectory of the phase difference of the interfering signal is tracked to remove the $2\pi$ ambiguity. A new interfering signal is required to track the trajectory of the phase difference. Specifically, in case of a coefficient of finesse smaller than 1 (F<1), the Airy function may be proximate to a cosine function according to the phase difference. The cosine function may be dependent on the phase difference. Accordingly, if a wavelength varies, the cosine function may change into a sine function. Thus, a cosine function at a first wavelength and a sine function at a second wavelength may specify the phase difference and a trajectory of the phase difference. In addition, the trajectory or a rotation direction of the phase difference may be decided. Thus, the $2\pi$ ambiguity may be removed from the phase difference. Accordingly, thickness variation of the transparent substrate may be decided. According to an embodiment of the present invention, thickness variation depending on position of a transparent substrate or relative thickness depending on position of a transparent substrate may be measured.

Preferred embodiments of the present invention will be described below in more detail with reference to the accompanying drawings. The present invention may, however, be embodied in different forms and should not be constructed as limited to the embodiments set forth herein. Rather, these embodiments are provided so that this disclosure will be thorough and complete, and will fully convey the scope of the invention to those skilled in the art. Like numerals refer to like elements throughout the specification.

Figure 1:
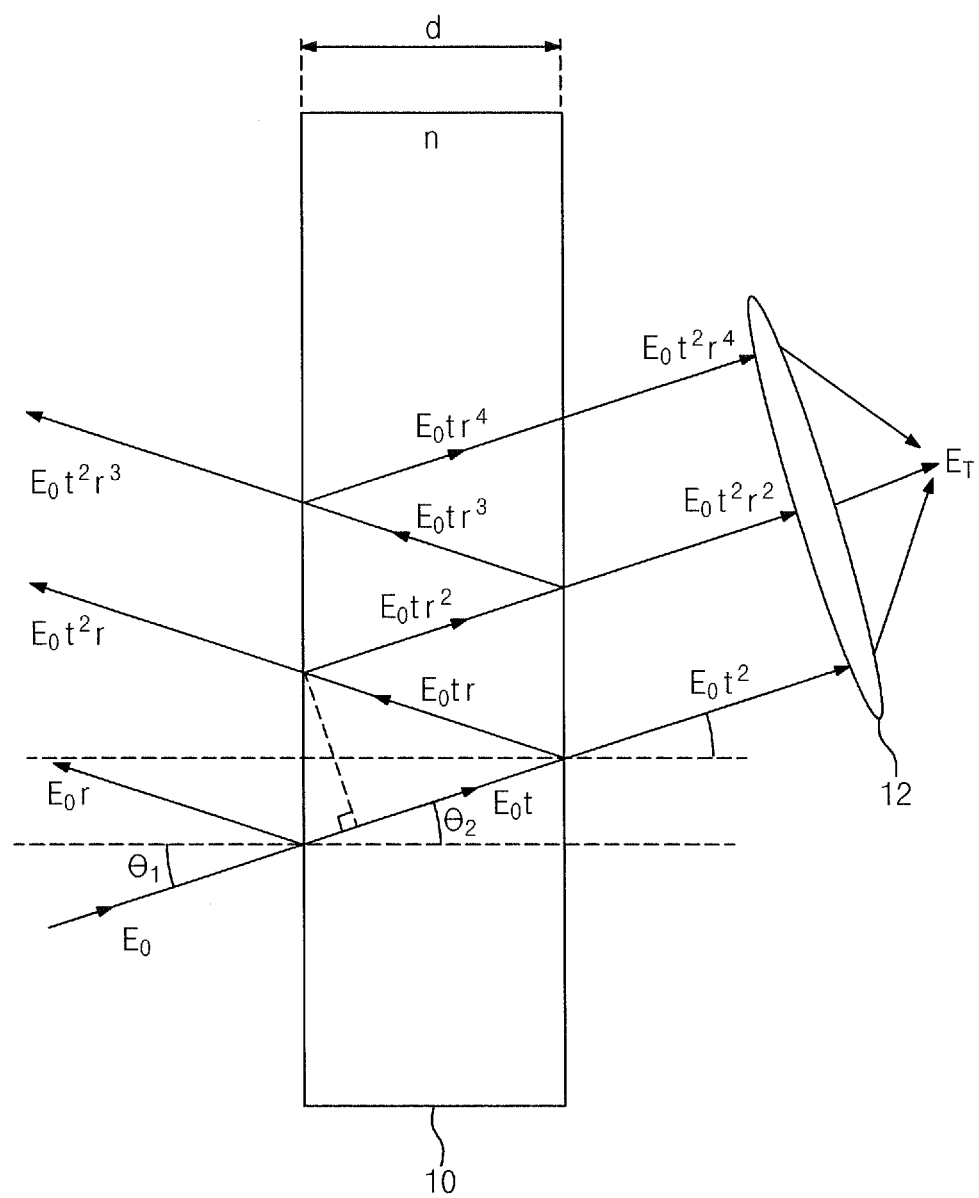
FIG. 1 illustrates a thickness measuring apparatus according to an embodiment of the present invention.

FIG. 1 illustrates a thickness measuring apparatus according to an embodiment of the present invention.

Referring to FIG. 1, a laser light source impinges on a transparent substrate 10. An incident angle of the laser light source is $\theta_1$, and a refraction angle of the laser light source is $\theta_2$. Thickness of the transparent substrate 10 is d, and a refractive index of the transparent substrate 10 is n. Let it be assumed that a refractive index of air is 1. The intensity of an electric field of an incident light is $E_0$. The incident light performs multiple internal reflection in the transparent substrate 10. A reflection coefficient on an incident plane and a transmission plane is r, and a transmission coefficient of transmitting the incident plane and the transmission plane is t. A wavelength of the laser light source in vacuum is $\lambda_1$.

In addition, $E_0 t^2$ and $E_0 r^2 t^2$ are adjacent rays. A difference in path phase between two adjacent rays ($\psi$) may be given as below.

$$\psi = \frac{4\pi}{\lambda_0} n d \cos(\theta_2) \qquad \text{Equation (1)}$$

An electric field of the total transmitted beam by multiple reflection may be focused through a focusing lens 12 and given as below.

$$E_T = E_0 t^2 + E_0 t^2 r^2 e^{i\psi} + E_0 t^2 r^4 e^{i2\psi} + \ldots \qquad \text{Equation (2)}$$

$$E_T = E_0 \frac{t^2}{1 - r^2 e^{i\psi}}$$

The intensity of the total transmitted beam may be given as an Airy function, as below.

$$I_T = I_0 \frac{t^4}{|1 - r^2 e^{i\psi}|^2} \qquad \text{Equation (3)}$$

$$r = |r| e^{i\frac{\psi_r}{2}}$$

$$R = |r|^2,$$

$$T = |t|^2,$$

$$\Psi = \psi + \psi_r$$

$$I_T = I_0 \frac{T^2}{(1-R)^2} \frac{1}{1 + \frac{4R}{(1-R)^2} \sin^2\left(\frac{\Psi}{2}\right)}$$

$$F = \frac{4R}{(1-R)^2}$$

In the Equation (3), $\psi_r/2$ represents reflection phase change by one-time reflection, R represents reflectance, T represents transmittance, $\Psi$ represents the total phase difference, and F represents a coefficient of finesse.

In the case that F<1, if the intensity of the transmitted beam is expanded using Taylor series expansion and secondary or higher series terms are neglected, the intensity of the transmitted beam may be expressed as below.

$$I_T \approx \frac{2I_0 T^2}{(2+F)(1-R)^2}\left(1 + \frac{F}{2+F}\cos\Psi\right) \qquad \text{Equation (4)}$$

The intensity of the transmitted beam is expressed as a cosine function to the total phase difference. On the other hand, a sine function to the intensity of the transmitted beam is required to track a trajectory of the total phase difference $\Psi$.

Two signals of $I_T(\Psi)$ and $I_T(\Psi+\pi/2)$ are needed to obtain the total phase difference from the intensity of the transmitted beam ($I_T$). For example, when a reflection phase change $\psi_r$ is zero, $I_T(\psi)$ and $I_T(\psi+\pi/2)$ are required. A cosine phase term of the transmitted beam is expressed as below.

$$\cos\psi = \cos\left(\frac{4\pi}{\lambda_1} n d \cos(\theta_2)\right) \qquad \text{Equation (5)}$$

If a first wavelength $\lambda_1$ changes into a second wavelength $\lambda_2$, $\psi$ may be made to change by $\pi/2$. Accordingly, the intensity of the transmitted beam may have a cosine function depending on thickness d of a transparent substrate at a first wavelength and have a sine function depending on the thickness d of the transparent thickness at a second wavelength. Thus, the trajectory of the phase difference may be tracked to remove $2\pi$ ambiguity of the phase difference.

Figure 2:
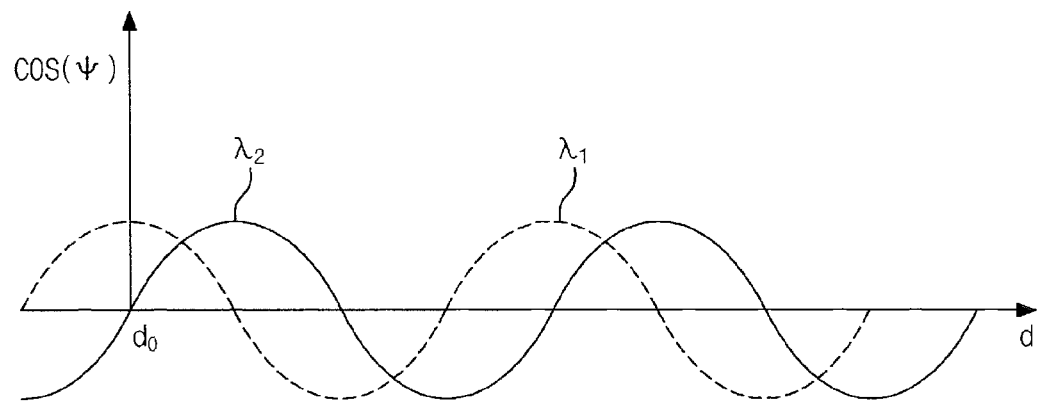
FIG. 2 is a graph showing $\cos(\psi)$ depending on thickness d of a substrate at predetermined first and second wavelengths $\lambda_1$ and $\lambda_2$.

FIG. 2 is a graph showing $\cos(\psi)$ depending on thickness d of a substrate at predetermined first and second wavelengths $\lambda_1$ and $\lambda_2$.

Referring to FIG. 2, the second wavelength $\lambda_2$ may be selected such that $\psi$ changes by $N\pi+\pi/2$ (N being an integer). For example, when the second wavelength $\lambda_2$ is selected such that $\psi$ changes by $\pi/2$, the second wavelength $\lambda_2$ may be given as below.

$$\frac{4\pi}{\lambda_2} n d \cos(\theta_2) = \frac{4\pi}{\lambda_1} n d \cos(\theta_2) - \frac{\pi}{2} \qquad \text{Equation (6)}$$

$$\lambda_2 = \lambda_1 + \Delta\lambda$$

$$\Delta\lambda \approx \frac{\lambda_1^2}{8nd\cos(\theta_2)}$$

On the other hand, the second wavelength $\lambda_2$ is dependent on the thickness d of the transparent substrate. Nonetheless, the thickness d of the transparent substrate is much greater than the first wavelength $\lambda_1$. Conventionally, thickness of the transparent substrate is about hundreds of micrometers and several micrometers of the first wavelength $\lambda_1$. Accordingly, an error of a period depending on thickness variation of the transparent substrate is negligible. When the first wavelength $\lambda_1$ is 1.5 micrometers, d is 700 micrometers, n is 1.5, and $\theta_2$ is 90 degrees, $\Delta\lambda$ may be 0.00027 micrometers. The $\Delta\lambda$ is much smaller than the first wavelength $\lambda_1$. Thus, a repetition period to thickness is substantially equal relative to the first wavelength $\lambda_1$ and the second wavelength $\lambda_2$.

Under the situation where thickness d varies, in case of $\lambda_1$ and $\lambda_2$ satisfying the condition of a phase change of $\pi/2$ at a phase term of a transmitted beam, the intensity of the transmitted beam may be given as below.

$$I_T(\lambda_1) = I_0^1\left[1 + \frac{F}{2+F}\cos\left(\frac{4\pi}{\lambda_1}nd\cos(\theta_2 0)\right)\right]$$ Equation (7)

$$I_T(\lambda_2) = I_0^2\left[1 + \frac{F}{2+F}\cos\left(\frac{4\pi}{\lambda_2}nd\cos(\theta_2 0)\right)\right]$$

$$I_T(\lambda_2) = I_0^2\left[1 + \frac{F}{2+F}\cos\left(\frac{4\pi}{\lambda_1}nd\cos(\theta_2 0)\right)\right]$$

$$I_0^1 = \frac{2I_0(\lambda_1)T^2}{(2+F)(1-R)^2}$$

$$I_0^2 = \frac{2I_0(\lambda_2)T^2}{(2+F)(1-R)^2}$$

In the equation (7), $I_T(\lambda_1)$ represents the intensity of the first transmitted beam at a first wavelength, $I_T(\lambda_2)$ represents the intensity of the second transmitted beam at a second wavelength. The $I_T(\lambda_1)$ includes a cosine function depending on thickness of a transparent substrate, and the $I_T(\lambda_2)$ includes a sine function depending on the thickness of the transparent substrate. In addition, $I_0^1$ and $I_0^2$ are constants.

Figure 3:
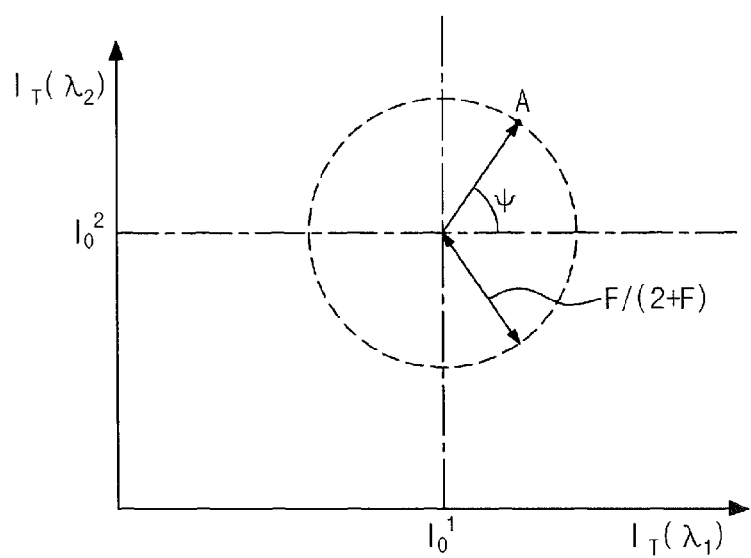
FIG. 3 is a Lissajous graph constructed by different axes of the intensity of a transmitted beam of a first wavelength and the intensity of a transmitted beam of a second wavelength.

FIG. 3 is a Lissajous graph constructed by different axes of the intensity of a transmitted beam of a first wavelength and the intensity of a transmitted beam of a second wavelength.

Referring to FIG. 3, a position A defined by the intensity $I_T(\lambda_1)$ of the transmitted beam of the first wavelength and the intensity $I_T(\lambda_2)$ of the transmitted beam of the second wavelength may perform circular motion or elliptical motion on the basis of a center point $(I_0^1, I_0^2)$. A rotation angle of the position A may be identical to the total phase difference $\Psi$. Accordingly, the position A may perform rotational motion on the Lissajous graph as thickness of a transparent substrate varies successively. Thus, the rotation angle may be tracked to calculate the thickness of the transparent substrate.

$$\tan\left(\frac{4\pi}{\lambda_1}nd\cos(\theta_2)\right) = \frac{I_0^1 I_T(\lambda_2) - I_0^2 I_0^1}{I_0^2 I_T(\lambda_1) - I_0^1 I_0^2}$$ Equation (8)

$$d = \frac{\lambda_1}{4\pi n\cos(\theta_2)}\tan^{-1}\left(\frac{I_0^1 I_T(\lambda_2) - I_0^2 I_0^1}{I_0^2 I_T(\lambda_1) - I_0^1 I_0^2}\right)$$

If the intensities $I_T(\lambda_1)$ and $I_T(\lambda_2)$ of the transmitted beams are detected at $\lambda_1$ and $\lambda_2$ satisfying the condition of the equation (6) and the equation (8) is used, thickness of a transparent substrate is calculated. The total rotation angle is given by $(M\times 2\pi+\Psi)$ (M being an integer indicating a rotation count). Thus, relative thickness D is given by $(D=d+M\times\lambda_1/(2n\cos(\theta_2)))$.

Figure 4:
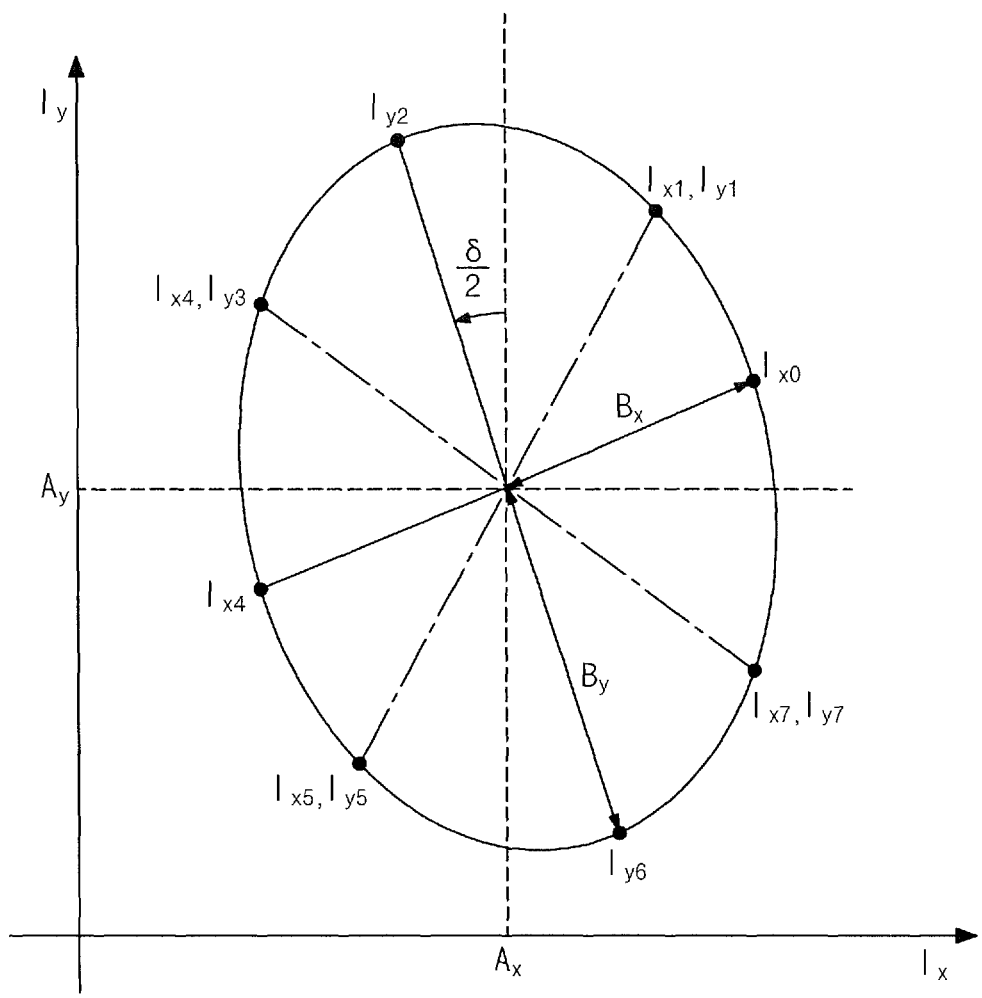
FIG. 4 shows a Lissajous graph.

FIG. 4 shows a Lissajous graph.

Referring to FIG. 4, a Lissajous graph of a measurement signal may get out of an ideal circle due to polarization mixing, laser intensity drift, instability of an electric circuit, and the like. Thus, a nonlinearity error is generated. First transmitted beam and second transmitted beam of the equation (7) may be converted into a measurement signal through an optical detector. Measurement signals Ix and Iy may be expressed as the equation (9).

$$I_x = A_x + B_x\cos\left(\phi + \frac{\delta}{2}\right)$$ Equation (9)

$$I_y = A_y + B_y\sin\left(\phi - \frac{\delta}{2}\right)$$

In the equation (9), $A_x$ and $A_y$ represent DC offsets, $B_x$ and $B_y$ represent AC amplitudes, $\delta$ represents a phase difference indicating the degree of getting out of 90 degrees, and $\varphi$ represents a phase difference proportional to thickness of a transparent substrate. The phase difference $\varphi$ may correspond to the total phase difference $\Psi$ in the equation (4).

Referring to the equation (8), a Lissajous graph of two measurement signals generally has an elliptical form, and a measured phase difference $\varphi$ may be calculated as below.

$$\phi = \tan^{-1}\left[\frac{\tan\frac{\delta}{2}B_y(I_x - A_x) + B_x(I_y - A_y)}{B_y(I_x - A_x) + \tan\frac{\delta}{2}B_x(I_y - A_y)}\right]$$ Equation (10)

Accordingly, parameter values $A_x$, $B_x$, $A_y$, $B_y$, and $\delta$ indicating two measurement signals must be accurately understood to accurately obtain a phase difference and thickness of a transparent substrate without a nonlinearity error.

Figure 5:
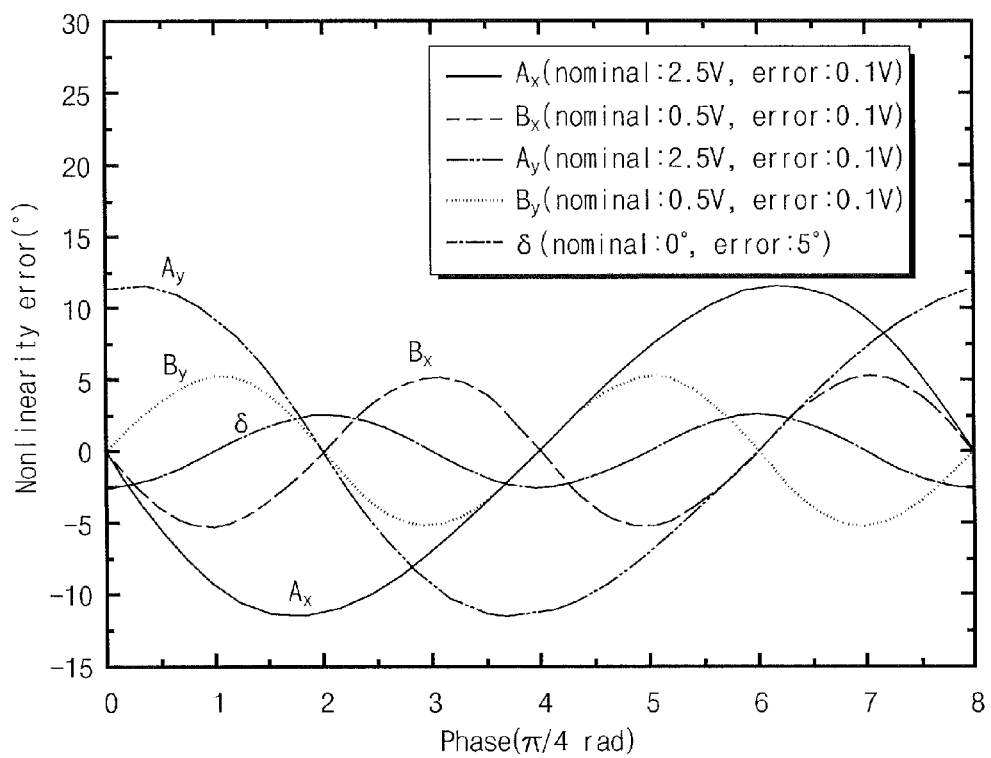
FIG. 5 is a graph showing a nonlinearity error of phase difference calculation caused by an estimation error of each parameter value.

FIG. 5 is a graph showing a nonlinearity error of phase difference calculation caused by an estimation error of each parameter value.

Referring to FIG. 5, the nonlinearity error exhibits a periodical characteristic and has a position where a size of the nonlinearity error repeatedly becomes zero.

When many parameters have an estimation error, a position where a nonlinearity error becomes zero is slightly changed. However, a nonlinearity error continues to keep a small value at a position where a phase difference $\varphi$ is a multiple of $\pi/4$. Thus, parameters may be accurately estimated using a measurement signal at the position where a phase difference $\varphi$ is a multiple of $\pi/4$.

Five parameters indicating two measurement signals may be obtained using twelve reference measurement signal values $I_{x0}$, $I_{x1}$, $I_{x3}$, $I_{x4}$, $I_{x5}$, $I_{x7}$; $I_{y1}$, $I_{y2}$, $I_{y3}$, $I_{y5}$, $I_{y6}$, and $I_{y7}$ at a position where a phase is $n\times\pi/4$ (n=0 ... 7).

The table (1) indicates twenty reference measurement signals used in calculation and is induced using the equation (9). The table (1) is displayed on the Lissajous graph in FIG. 7.

TABLE 1

| n | $I_{xn}$ | $I_{yn}$ |
|---|---|---|
| 0 | $A_x + B_x\cos\frac{\delta}{2}$ | — |
| 1 | $A_x + \frac{B_x}{\sqrt{2}}\cos\frac{\delta}{2} - \frac{B_x}{\sqrt{2}}\sin\frac{\delta}{2}$ | $A_y + \frac{B_y}{\sqrt{2}}\cos\frac{\delta}{2} - \frac{B_y}{\sqrt{2}}\sin\frac{\delta}{2}$ |
| 2 | — | $A_y + B_y\cos\frac{\delta}{2}$ |
| 3 | $A_x - \frac{B_x}{\sqrt{2}}\cos\frac{\delta}{2} - \frac{B_x}{\sqrt{2}}\sin\frac{\delta}{2}$ | $A_y + \frac{B_y}{\sqrt{2}}\cos\frac{\delta}{2} + \frac{B_y}{\sqrt{2}}\sin\frac{\delta}{2}$ |
| 4 | $A_x - B_x\cos\frac{\delta}{2}$ | — |
| 5 | $A_x - \frac{B_x}{\sqrt{2}}\cos\frac{\delta}{2} + \frac{B_x}{\sqrt{2}}\sin\frac{\delta}{2}$ | $A_y - \frac{B_y}{\sqrt{2}}\cos\frac{\delta}{2} + \frac{B_y}{\sqrt{2}}\sin\frac{\delta}{2}$ |
| 6 | — | $A_y - B_y\cos\frac{\delta}{2}$ |

TABLE 1-continued

| n | $I_{xn}$ | $I_{yn}$ |
|---|---|---|
| 7 | $A_x + \dfrac{B_x}{\sqrt{2}}\cos\dfrac{\delta}{2} + \dfrac{B_x}{\sqrt{2}}\sin\dfrac{\delta}{2}$ | $A_y - \dfrac{B_y}{\sqrt{2}}\cos\dfrac{\delta}{2} - \dfrac{B_y}{\sqrt{2}}\sin\dfrac{\delta}{2}$ |

Five parameter values may be calculated as below.

$$A_x = \frac{I_{x0} + I_{x4}}{2}$$

$$B_x \cos\left(\frac{\delta}{2}\right) = \frac{I_{x0} - I_{x4}}{2}$$

$$A_y = \frac{I_{y2} + I_{y6}}{2}$$

$$B_y \cos\left(\frac{\delta}{2}\right) = \frac{I_{y2} - I_{y6}}{2}$$

$$\tan\frac{\delta}{2} = \frac{(-I_{x3} + I_{y3} + I_{x7} - I_{x7}) - (I_{x1} + I_{y1} - I_{x5} - I_{y5})}{(-I_{x3} + I_{y3} + I_{x7} - I_{y7}) + (I_{x1} + I_{y1} - I_{x5} - I_{y5})}$$

Equation (11)

Each parameter was calculated using only reference measurement signals at a phase where an influence of an estimation error of each parameter to a nonlinearity error is minimized.

These parameters are updated whenever a phase difference matches a multiple of π/4, and a phase difference Ψ proportional to thickness d of a transparent substrate or a phase difference φ is calculated using an updated parameter. Thus, a more accurate phase difference may be obtained in the next step, and an estimation error of a parameter using the obtained phase difference may decrease. Since this correction procedure is repeatedly executed, the estimation error of a parameter may decrease according to the number of repetitions and a nonlinearity error caused by the estimation error of a parameter value may be removed. Moreover, since the parameter value may be obtained through simple arithmetical calculation, the nonlinearity error may be corrected in real time.

A digital signal processing module for real-time correction of nonlinearity of a thickness measuring apparatus may be implemented using a field programmable gate array (FPGA). A used data acquisition board (NI PCI-7831R, National Instruments) may be synchronized with a reconfigurable input/output unit with high precision. The board may include a 16-bit analog-to-digital converter (ADC) of eight channels having sampling speed of 200 KHz and perform synchronous control with resolution of 25 nanoseconds (ns).

Figure 6:
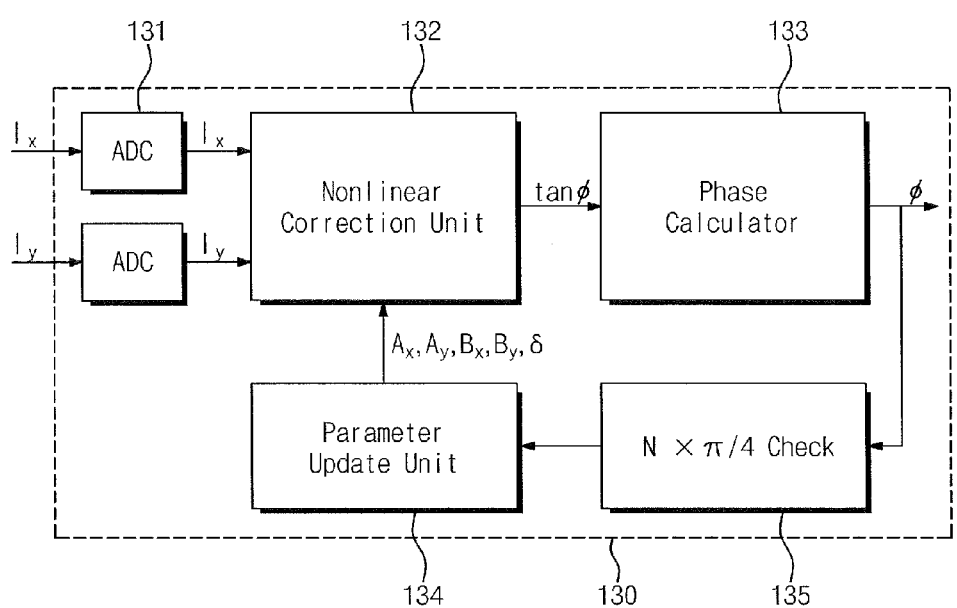
FIG. 6 illustrates the configuration of a processing unit using FPGA.

FIG. 6 illustrates the configuration of a processing unit using FPGA.

Referring to FIG. 6, a processing unit 130 may include an AD converter 131 converting a first measurement signal $I_x$ and a second measurement signal $I_y$ to digital signals, a nonlinear correction unit 132 performing nonlinear correction using the digitally converted first and second measurement signals, a parameter update unit 134 updating a parameter, and a check point confirm unit 135, and a phase calculator 133.

The nonlinear correction unit 132 may calculate a nonlinearly corrected phase output value tan(φ) using the two measurement signals $I_x$ and $I_y$ obtained from the AD converter 131 and parameter estimation values $A_x$, $B_x$, $A_y$, $B_y$, and δ. A parameter of an arctangent in the equation (10) is calculated using the obtained measurement signals $I_x$ and $I_y$ and the parameter estimation values $A_x$, $B_x$, $A_y$, $B_y$, and δ. Calculation of a phase φ using the arctangent function may be performed by a phase calculator 133 using a look-up table (LTU). The phase φ may be calculated by equally dividing a 2π phase range into 1024 parts.

The check point confirm unit 135 confirms whether a phase difference calculated during each phase calculation becomes integer multiple of π/4. When this condition is satisfied, parameters are updated using the equation (11). The updated parameters are stored in the parameter update unit 134 and used in the next-time nonlinear correction.

In this procedure, an additional procedure may be introduced to reduce the accidental effect of a parameter estimation value caused by noise of a measurement signal that corresponds to a phase shift of high speed and is measured. Since a measurement signal varies very fast during high-speed thickness measurement, it is difficult to detect a position where a phase difference becomes an integer multiple of π/4. Thus, a tolerance may be introduced to adjust a standard of judgment for such a check point.

Figure 7:
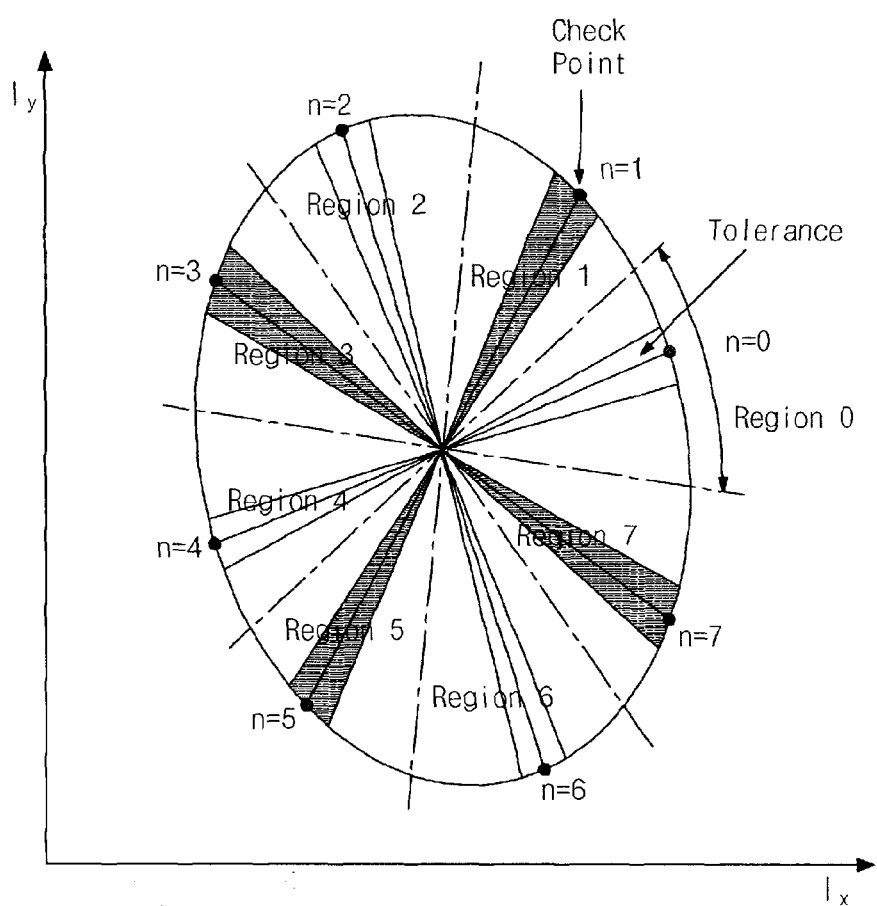
FIG. 7 is a graph to set a tolerance in a Lissajous trajectory.

FIG. 7 is a graph to set a tolerance in a Lissajous trajectory.

Referring to FIG. 7, it is easier to detect a check point as a tolerance becomes wider. However, since all phase values within the tolerance are judged to be a check point, accuracy of a parameter estimation value is reduced. As the tolerance becomes narrower, an opposite tendency emerges. Thus, a method of adjusting a tolerance according to speed of displacement under measurement may be applied.

If a parameter estimation value is calculated only using a measurement signal value of a single check point, noise of an obtained phase signal has an influence on accuracy of the parameter estimation value. Not only a tolerance but also a sub-sectional region is introduced to reduce such an accidental effect.

The sub-sectional region is formed by dividing the total 2π phase into eight regions whose center is n×π/4 and range is (2n±1)>π/8. When a phase value reaches a set check point, a parameter value is not directly updated using a phase signal value but is updated to a new parameter value using an average of parameter estimation values obtained by accumulating a phase value until the phase value gets out of a currently belonging sub-sectional region. Accordingly, this method may prevent noise of a phase signal from occurring due to an accidental effect of the parameter estimation value.

Figure 8:
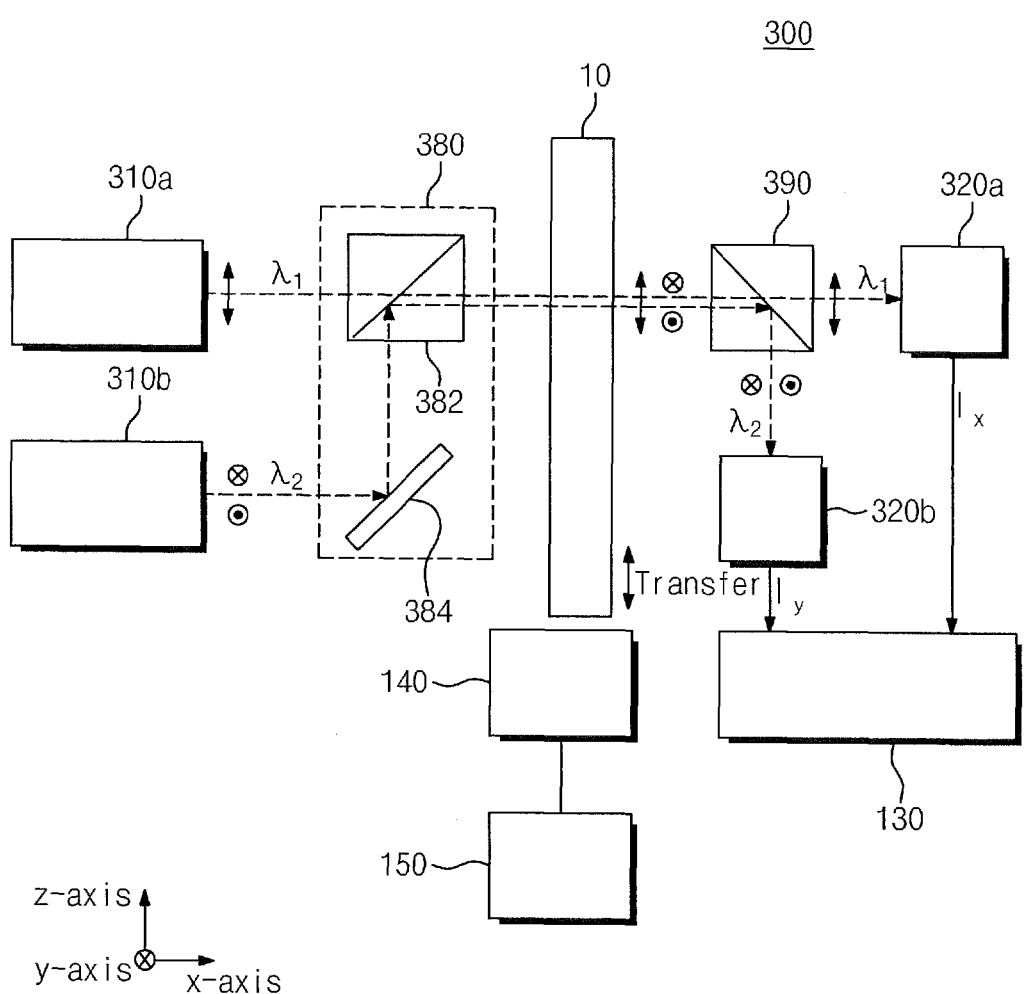
FIGS. 8 to 12 illustrate thickness measuring apparatuses according to embodiments of the present invention.

FIG. 8 illustrates a thickness measuring apparatus according to an embodiment of the present invention.

Referring to FIG. 8, a thickness measuring apparatus 300 includes a first laser 310a outputting a laser beam of a first wavelength, a second laser 310b outputting a laser beam of a second wavelength, an optical coupler 380 coupling an output of the first laser 310a and an output of the second laser 310b with each other and providing the combined output to a first position of a transparent substrate 10, a dichromatic beam splitter 390 splitting the first transmitted beam of the first wavelength and the second transmitted beam of the second wavelength from each other, a first optical detector 320a measuring the first transmitted beam of the first wavelength split through the dichromatic beam splitter 390, a second optical detector 320b measuring the second transmitted beam of the second wavelength split through the dichromatic beam splitter 390, and a processing unit 130. The processing unit 130 extracts a rotation angle on a Lissajous graph using intensity of the first transmitted beam of the first wavelength and intensity of the second transmitted beam of the second wavelength, a difference in optical path length between adjacent rays caused by internal reflection of the transparent substrate 10 at the first position, or a phase difference between adjacent rays caused by the internal reflection of the transparent substrate 10 at the first position.

Referring to the equation (7), the intensity of the first transmitted beam of the first wavelength may have a cosine function according to the phase difference, and the intensity of the second transmitted beam of the second wavelength may have a sine function according to the phase difference.

The first laser 310a may output a beam traveling in the x-axis direction and linearly polarized in the z-axis direction. The first laser 310a may be a variable laser diode. The second laser 310b may output a beam linearly polarized in the y-axis direction. The second laser beam 310b may be a variable laser diode. The second wavelength of the second laser 310a and the first wavelength of the first laser 310b may satisfy the condition of the equation (6). A wavelength band of the first laser 310a and the second laser 310b may be a visible ray region or an infrared region.

The optical coupler 380 may include a beam splitter 382 transmitting the laser beam of the first wavelength and reflecting the laser beam of the second wavelength and a reflection mirror 384 reflecting the laser beam of the second wavelength and providing the reflected laser beam to the beam splitter 382. The beam splitter 382 may be a polarization beam splitter. The beam splitter 382 may receive and transmit a first laser beam traveling in the x-axis direction and linearly polarized in the z-axis direction and may receive a second laser beam traveling in the z-axis direction and linearly polarized in the y-axis direction and refract the received second laser beam at 90 degrees to travel in the x-axis direction. Thus, the beam splitter 382 may couple the first laser beam and the second laser beam having two different polarizations to output beams having the same path. The beam coupled by the beam splitter 382 may be irradiated to the same position of the transparent substrate 10.

The dichromatic beam splitter 390 may be a polarization beam splitter. The dichromatic beam splitter 390 may be the first transmitted beam linearly polarized in the z-axis direction. The dichromatic beam splitter 390 may receive the second transmitted beam linearly polarized in the y-axis direction and refract the received second transmitted beam at 90 degrees in a negative z-axis direction.

A focusing lens (not shown) may be disposed between the dichromatic beam splitter 390 and the first optical detector 320a. In addition, a focusing lens (not shown) may be disposed between the dichromatic beam splitter 390 and the second optical detector 320b.

The first optical detector 320a may measure the intensity of the first transmitted beam of the first wavelength. The second optical detector 320b may measure the intensity of the second transmitted beam of the second wavelength. A first measurement signal $I_x$ of the first optical detector 320a and a second measurement signal $I_y$ of the second optical detector 320b may be processed by the processing unit 130. Each of the first and second optical detectors 320a and 320b may be a photodiode.

A transfer unit 130 may transfer the transparent substrate 10, and a transfer driving unit 150 may drive the transfer unit 130. The transfer unit 130 may be a transferring roller device or a vacuum adsorption transfer device. The processing unit 130 may calculate thickness variation depending on a position of the transparent substrate 10. When a difference between the first wavelength and the second wavelength is small, polarization-type beam splitting and coupling may be suitable.

The transparent substrate 10 may be transferred at constant speed. In this case, the transfer unit 130 may transfer the transparent substrate 10 in the z-axis direction. The transfer unit 130 may be a transferring roller or a vacuum adsorption transfer device. The transfer driving unit 150 may drive the transfer unit 130.

As the transparent substrate 10 is transferred, a measurement position may be changed. The first measurement signal and the second measurement signal may be signals obtained at different positions as the transparent substrate 10 is transferred. However, the transfer speed of the transparent substrate 10 may be controlled such that generation positions of the first measurement signal and the second measurement signal are substantially identical to each other.

According to a modified embodiment of the present invention, the transfer unit 130 may repeatedly perform a transfer operation and a stop operation, and the first measurement signal and the second measurement signal may be measured under a stop state.

As the transparent substrate 10 is transferred, a plurality of first measurement signals and a plurality of second measurement signals are generated. These measurement signals may rotate on a Lissajous graph. When a difference in rotation angle between adjacent measurement positions is greater than $2\pi$ or a difference in thickness between adjacent measurement positions is greater than $\lambda_1/2$, it may be difficult to track the trajectory of the rotation angle. Therefore, the difference in thickness between adjacent measurement positions may be maintained within a half wavelength $\lambda_1/2$.

Returning to FIG. 6, the processing unit 130 may include an AD converter 131 converting a first measurement signal $I_x$ and a second measurement signal $I_y$ to digital signals, a nonlinear correction unit 132 performing nonlinear correction using the digitally converted first and second measurement signals, a parameter update unit 134 updating a parameter, and a check point confirm unit 135, and a phase calculator 133.

According to the modified embodiment of the present invention, the first laser and the second laser may be replaced with single wavelength-variable laser. The wavelength-variable laser may be a wavelength-variable laser diode.

Figure 9:
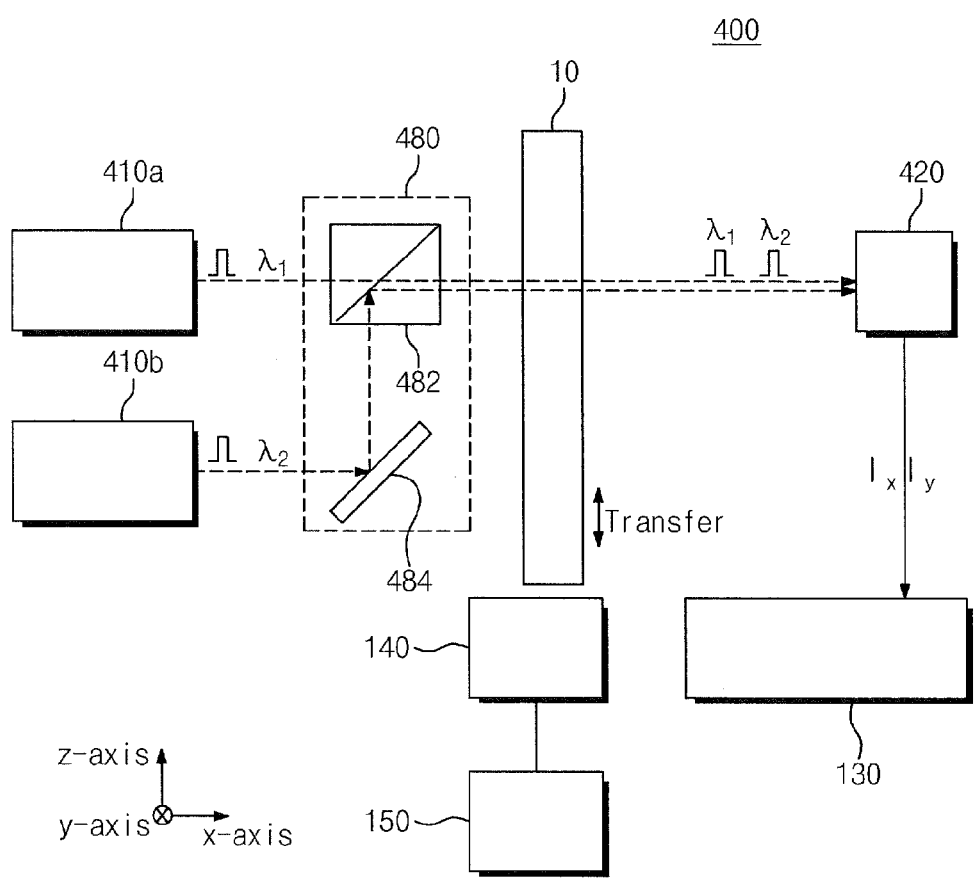

FIG. 9 illustrates a thickness measuring apparatus according to another embodiment of the present invention.

Referring to FIG. 9, a thickness measuring apparatus 400 includes a first laser 410a outputting a first pulse beam having a first wavelength and a first period, a second laser 410b outputting a second pulse beam oscillating at different time from the first pulse beam and having a second wavelength and the first period, an optical coupler 480 providing an output of the first laser 410a or an output of the second laser 410b to a first position of a transparent substrate 10, an optical detector 420 sequentially measuring a first transmitted beam of the first wavelength and second transmitted beams of the second wavelength transmitting through the transparent substrate 10, and a processing unit 130.

The processing unit 130 extracts a rotation angle on a Lissajous graph using intensity of the first transmitted beam of the first wavelength and intensity of the second transmitted beam of the second wavelength, a difference in optical path length between adjacent rays caused by internal reflection of the transparent substrate 10 at the first position, or a phase difference between adjacent rays caused by the internal reflection of the transparent substrate 10 at the first position.

Referring to the equation (7), the intensity of the first transmitted beam of the first wavelength may have a cosine function according to the phase difference, and the intensity of the second transmitted beam of the second wavelength may have a sine function according to the phase difference. The first wavelength $\lambda_1$ and the second wavelength $\lambda_2$ may satisfy the condition of the equation (6).

Time width of the first pulse beam of the first laser 410a may be smaller than the first period. In addition, time width of the second pulse beam of the second laser 410b may be smaller than the first period. In addition, the first pulse beam and the second pulse beam may be synchronized with each other and may oscillate at different times. Thus, the optical detector 420 may output a first measurement signal $I_x$ by the first pulse beam and a second measurement signal $I_y$ by the second pulse beam at different times. A pair of adjacent first and second pulse beams may be provided at substantially the same position of the transparent substrate 10. Thus, the first measurement signal $I_x$ by the first pulse beam and the second measurement signal $I_y$ by the second pulse beam may be provided to the processing unit 130. The processing unit 130 may calculate thickness of the transparent substrate 10 using the first measurement signal $I_x$ and the second measurement signal $I_y$.

The optical coupler 480 may include a beam splitter 482 transmitting the first pulse beam of the first wavelength and reflecting the second pulse beam of the second wavelength and a reflection mirror 484 reflecting the second pulse beam of the second wavelength and providing the reflected second pulse beam to the beam splitter 482.

A transfer unit 140 may transfer the transparent substrate 10, and a transfer driving unit 150 may drive the transfer unit 140.

Figure 10:
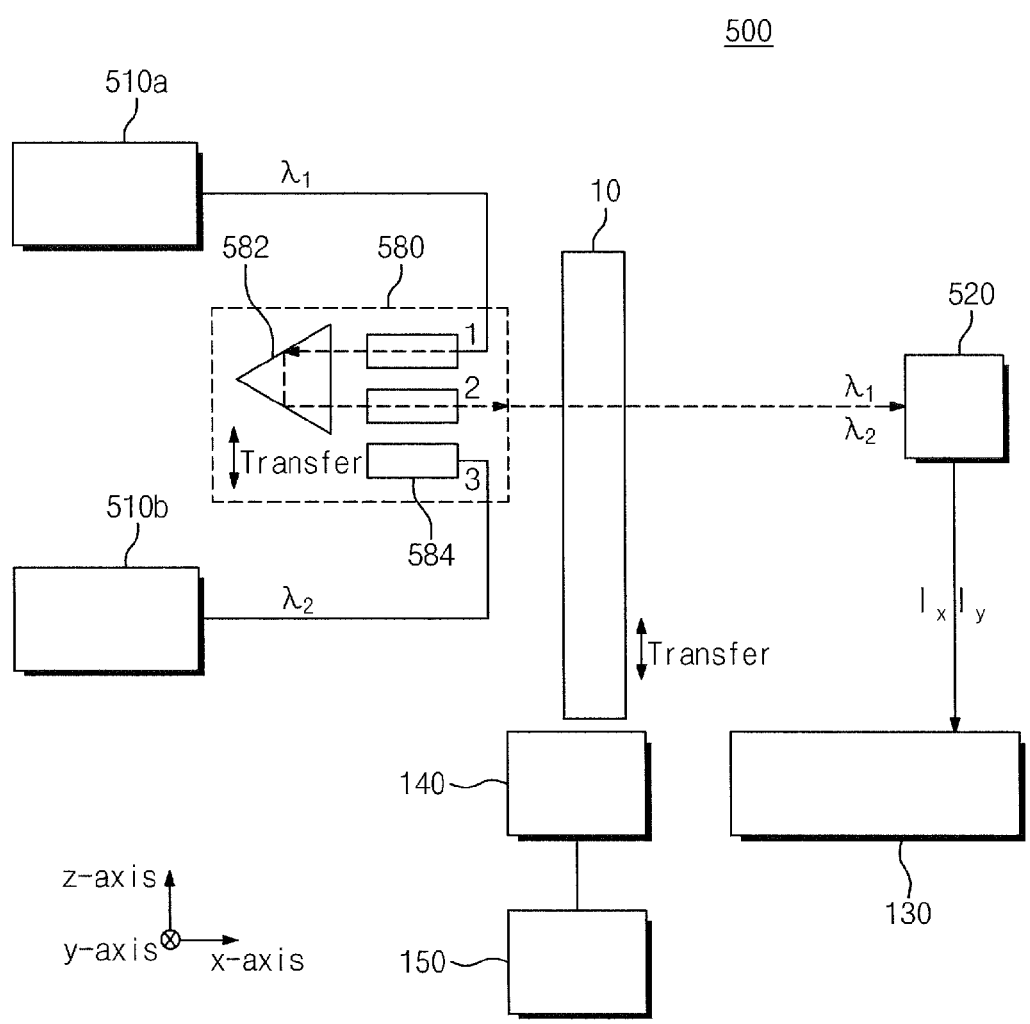

FIG. 10 illustrates a thickness measuring apparatus according to another embodiment of the present invention.

Referring to FIG. 10, a thickness measuring apparatus 500 includes a first laser 510a outputting a laser beam of a first wavelength, a second laser 510b outputting a laser beam of a second wavelength, an optical switch 580 receiving an output of the first laser 510a and an output of the second laser 510b and periodically and alternately providing the first laser beam and the second laser beam to a first position of a transparent substrate 10, an optical detector 520 measuring a first transmitted beam of the first wavelength or second transmitted beams of the second wavelength transmitting through the transparent substrate 10, and a processing unit 130. The processing unit 130 extracts a rotation angle on a Lissajous graph using intensity of the first transmitted beam of the first wavelength and intensity of the second transmitted beam of the second wavelength, a difference in optical path length between adjacent rays caused by internal reflection of the transparent substrate 10 at the first position, or a phase difference between adjacent rays caused by the internal reflection of the transparent substrate 10 at the first position.

Referring to the equation (7), the intensity of the first transmitted beam of the first wavelength may have a cosine function according to the phase difference, and the intensity of the second transmitted beam of the second wavelength may have a sine function according to the phase difference. The first wavelength $\lambda_1$ and the second wavelength $\lambda_2$ may satisfy the condition of the equation (6).

The optical switch 580 may be an optical switch of a 2×1 structure having a second input port and a first output port. The optical switch 580 may be a mechano-optical switch or an electro-optical switch. For example, the optical switch 580 may include a single prism 582 and three Grin lenses 584. The prism 582 may be mechanically moved by an electromagnet or the like. Thus, the optical switch 580 may selectively provide light provided to a first input port 1 or a second input port 2 to an output port 3

A transfer unit 140 may transfer the transparent substrate 10, and a transfer driving unit 150 may drive the transfer unit 140.

Figure 11:
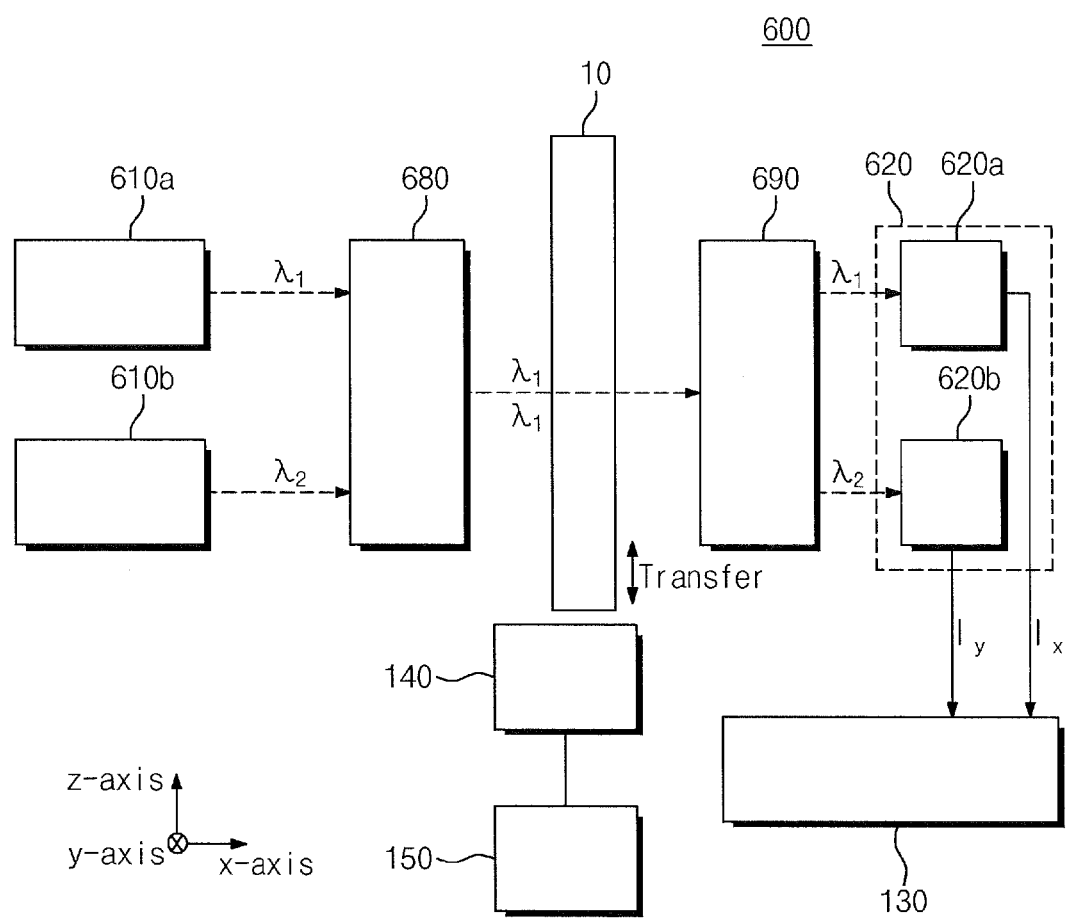

FIG. 11 illustrates a thickness measuring apparatus according to another embodiment of the present invention.

Referring to FIG. 11, a thickness measuring apparatus 600 includes a first laser 610a outputting a first laser beam of a first wavelength, a second laser 610b outputting a second laser beam of a second wavelength, a wavelength-division multiplexer 680 receiving and multiplexing the first laser beam and the second laser beam into a single output and providing the single output to a first position of a transparent substrate 10, an optical detector 620 measuring a first transmitted beam of the first wavelength or second transmitted beams of the second wavelength transmitting through the transparent substrate 10, and a processing unit 130.

The processing unit 130 extracts a rotation angle on a Lissajous graph using intensity of the first transmitted beam of the first wavelength and intensity of the second transmitted beam of the second wavelength, a difference in optical path length between adjacent rays caused by internal reflection of the transparent substrate 10 at the first position, or a phase difference between adjacent rays caused by the internal reflection of the transparent substrate 10 at the first position.

A wavelength-division demultiplexer 690 may be disposed between the transparent substrate 10 and the optical detector 620. The wavelength-division demultiplexer 690 receives the first transmitted beam and the second transmitted beam through a single input port, outputs the first transmitted beam of the first wavelength to a first output port, and outputs the second transmitted beam of the second wavelength to a second output port.

The optical detector 620 includes a first optical detector 620a and a second optical detector 620b. The first optical detector 620a is connected to the first output port of the wavelength-division demultiplexer 690, and the second optical detector 620b is connected to the second output port of the wavelength-division demultiplexer 690.

A transfer unit 140 may transfer the transparent substrate 10, and a transfer driving unit 150 may drive the transfer unit 140.

Figure 12:
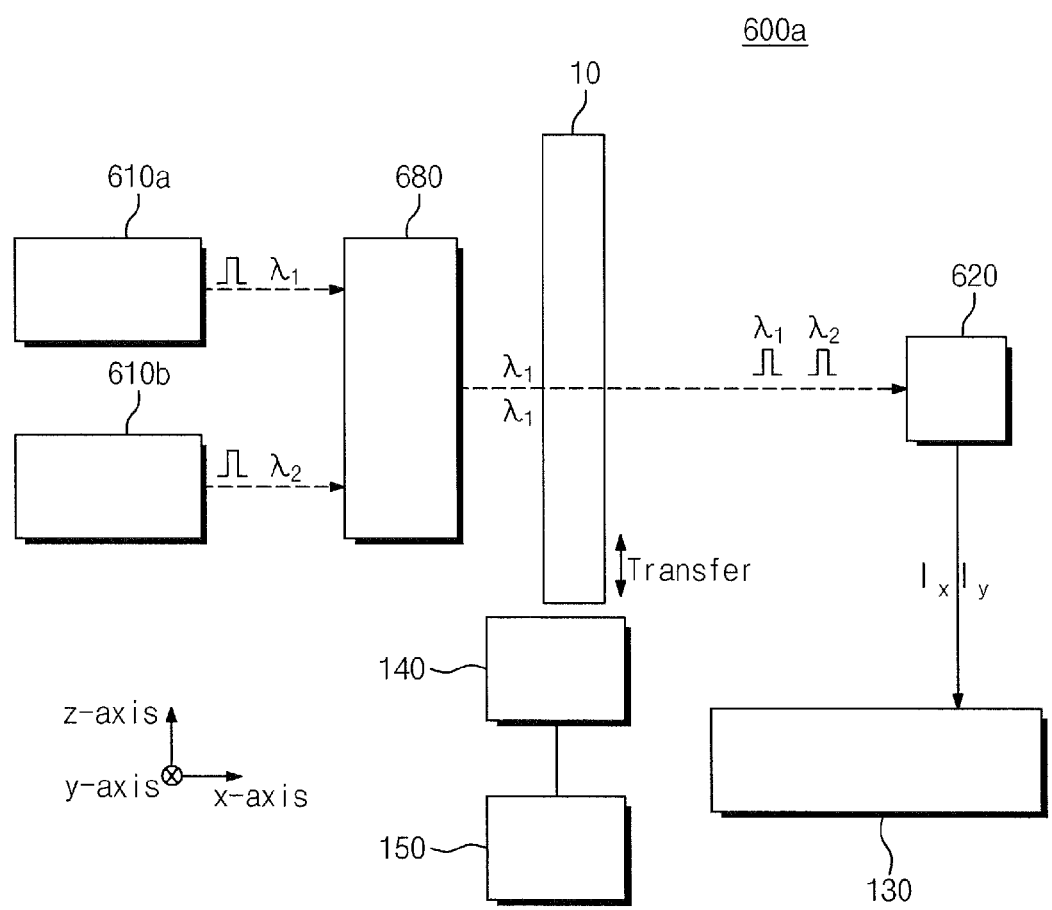

FIG. 12 illustrates a thickness measuring apparatus according to another embodiment of the present invention.

Referring to FIG. 12, a thickness measuring apparatus 600a includes a first laser 610a outputting a first laser beam of a first wavelength, a second laser 610b outputting a second laser beam of a second wavelength, a wavelength-division multiplexer 680 receiving and multiplexing the first laser beam and the second laser beam into a single output and providing the single output to a first position of a transparent substrate 10, an optical detector 620 measuring a first transmitted beam of the first wavelength or second transmitted beams of the second wavelength transmitting through the transparent substrate 10, and a processing unit 130.

The processing unit 130 extracts a rotation angle on a Lissajous graph using intensity of the first transmitted beam of the first wavelength and intensity of the second transmitted beam of the second wavelength, a difference in optical path length between adjacent rays caused by internal reflection of the transparent substrate 10 at the first position, or a phase difference between adjacent rays caused by the internal reflection of the transparent substrate 10 at the first position.

The first laser beam of the first laser and the second laser beam of the second laser may be in form of a periodical pulse. The first laser beam and the second laser beam may not temporally overlap each other. Accordingly, the optical detector 620 may measure alternate first pulse beam of the first wavelength and second pulse beam of the second wavelength. The optical detector 620 may output a first measurement signal $I_x$ corresponding to the first pulse beam and a second measurement signal $I_y$ corresponding to the second pulse beam according to time.

A transfer unit 140 may transfer the transparent substrate 10, and a transfer driving unit 150 may drive the transfer unit 140.

Figure 13:
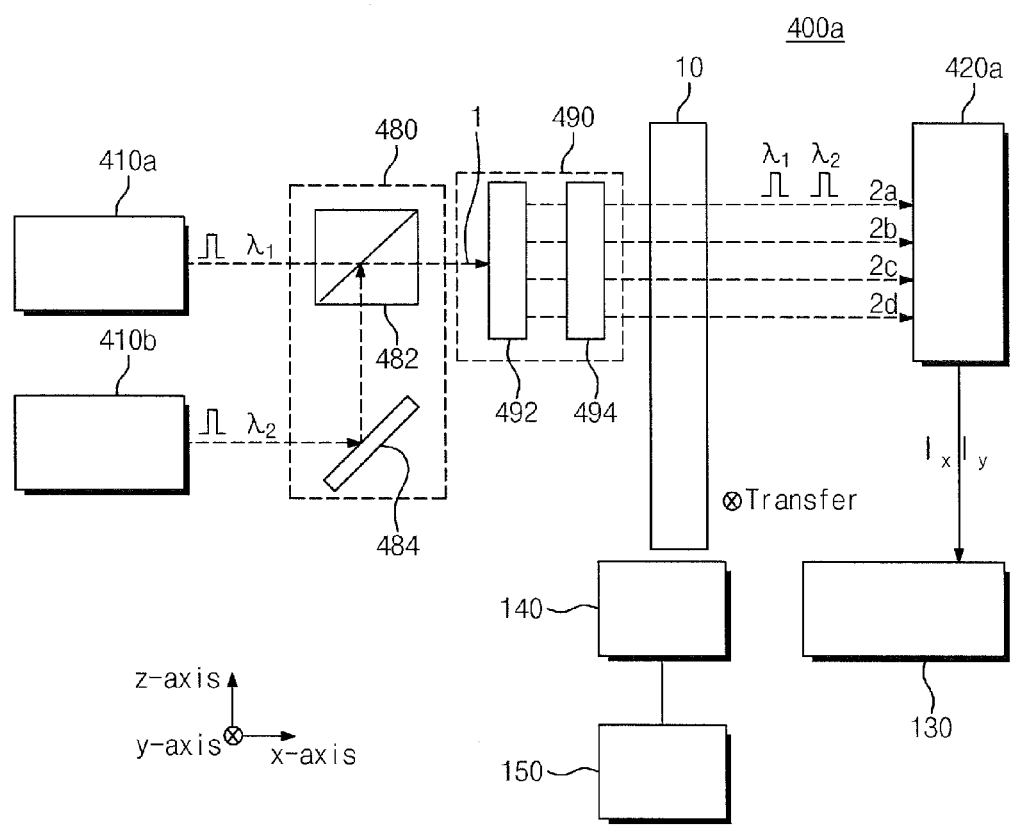
FIG. 13 is a thickness measuring apparatus according to another embodiment of the present invention.

FIG. 13 is a thickness measuring apparatus according to another embodiment of the present invention.

Figure 14:
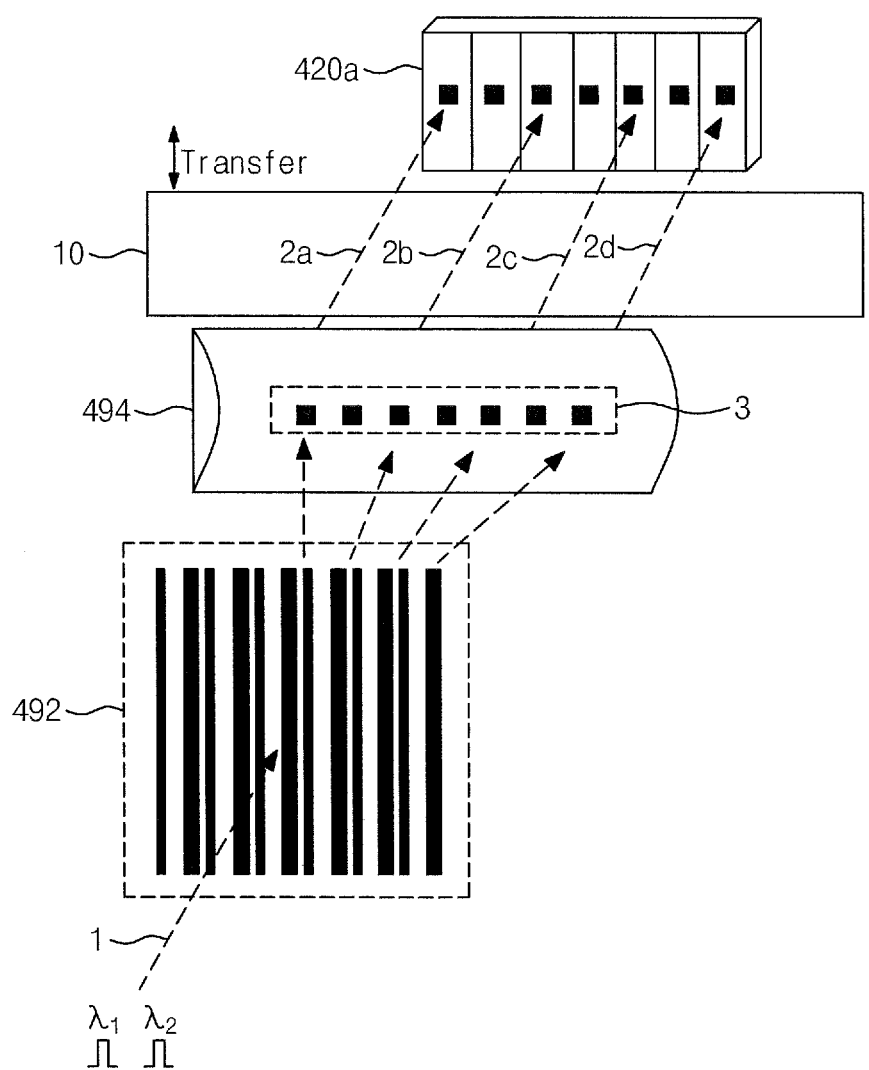
FIG. 14 is a perspective view of a pattern beam generator in FIG. 13.

FIG. 14 is a perspective view of a pattern beam generator in FIG. 13.

Referring to FIGS. 13 and 14, a thickness measuring apparatus 400a includes a first laser 410a outputting a first laser beam of a first wavelength, a second laser 410b outputting a second laser beam of a second wavelength, an optical coupler 480 receiving and outputting the first laser beam and the second beam to a single path, a pattern beam generator 490 disposed between the optical coupler 480 and a transparent substrate 10 to generate pattern beam 3, an optical detector array 420a measuring the first transmitted beam of the first wavelength and the second transmitted beam of the second wavelength transmitting through the transparent substrate 10, and a processing unit 130. The processing unit 130 extracts a rotation angle on a Lissajous graph using intensity of the first transmitted beam of the first wavelength and intensity of the second transmitted beam of the second wavelength, a difference in optical path length between adjacent rays caused by internal reflection of the transparent substrate 10 at the first position, or a phase difference between adjacent rays caused by the internal reflection of the transparent substrate 10 at the first position.

The pattern beam generator 190 includes a diffraction grating element 492 diffracting received beam 1 to generate a plurality of beams aligned in a constant direction and a collimation lens 494 converting a ray transmitting through the diffraction grating element 492 to parallel rays 2a to 2d. The diffraction grating element 492 may be a binary phase fanout grating aligned in a constant direction to generate a pattern beam 3 in a direction intersecting a transfer direction of the transparent substrate 10. The collimation lens 494 may be a cylindrical lens.

The first laser 410a outputs a pulse-type first laser beam, the second laser 410b outputs a pulse-type second laser beam, and the first laser beam 410a and the second laser beam 410b do not impinge on the transparent substrate 10 at the same time. Accordingly, the first transmitted beam by the first laser beam and the second transmitted beam by the second laser beam are detected with time interval by the optical detector array 420a. Thus, thickness may be measured at a plurality of positions.

According to a modified embodiment of the present invention, the diffraction grating element 492 may be a two-dimensional grating to form a matrix-type pattern. The collimation lens 494 may be a spherical lens.

According to a modified embodiment of the present invention, the first laser 410a and the second laser 410b may be replaced with a single wavelength-variable laser. Thus, the optical coupler 480 may be removed.

According to a thickness measuring apparatus and a thickness measuring method described above, a first wavelength and a second wavelength transmit through a transparent substrate and the transmitted beam is measured to easily measure thickness variation of the transparent substrate. In particular, the thickness measuring apparatus may stably measure thickness of a substrate even under an environment, such as a transfer roller, causing vibration or an environment in which a substrate is generally warped.

Although the present invention has been described in connection with the embodiment of the present invention illustrated in the accompanying drawings, it is not limited thereto. It will be apparent to those skilled in the art that various substitutions, modifications and changes may be made without departing from the scope and spirit of the present invention.

What is claimed is:

1. A thickness measuring method comprising:
    measuring an intensity of a first transmitted beam of a first wavelength transmitting at a first measurement position of a transparent substrate;
    expanding an Airy function using Taylor series expansion under a condition in which a coefficient of finesse is smaller than 1, such that the first transmitted beam of the first wavelength transmitted through the transparent substrate given as an Airy function is represented as a cosine function to a phase difference caused by optical path length between adjacent rays transmitted through multiple internal reflection of the transparent substrate;
    selecting a second wavelength to transform the cosine function into a sine function;
    measuring an intensity of a second transmitted beam of the second wavelength transmitting at the first measurement position of the transparent substrate;
    processing the intensity of the first transmitted beam and the intensity of the second transmitted beam to extract a rotation angle on a Lissajous graph; and
    calculating a thickness of the transparent substrate using the rotation angle.

2. The thickness measuring method of claim 1, further comprising changing a measurement position of the transparent substrate and repeating the thickness measuring method at a second measurement position.

3. The thickness measuring method of claim 1, further comprising removing a nonlinearity error from the rotation angle.

4. The thickness measuring method of claim 1, further comprising:
    converting a first measurement signal of the first laser beam and a second measurement signal of the second laser beam from analog to digital first and second measurement signals;
    performing a nonlinear correction using the digital first and second measurement signals;
    confirming whether a phase difference corresponding to the rotation angle calculated during each phase calculation becomes integer multiple of $\pi/4$;
    updating and storing a parameter when the phase difference corresponding to the rotation angle is integer multiple of $\pi/4$; and
    calculating the phase difference corresponding to the rotation angle.

5. A thickness measuring method comprising:
    measuring a first measurement signal of a first transmitted beam of a first wavelength $\lambda 1$ transmitting at a first position relative to a transparent substrate;

measuring a second measurement signal of a second transmitted beam of a second wavelength λ2 transmitting at the first position relative to the transparent substrate;

processing the first measurement signal and the second measurement signal to extract a rotation angle on a Lissajous graph; and calculating thickness of the transparent substrate using the rotation angle, wherein the first wavelength and the second wavelength satisfy a condition below:

$$\frac{4\pi}{\lambda_2}nd\cos(\theta_2) = \frac{4\pi}{\lambda_1}nd\cos(\theta_2) - \frac{\pi}{2}$$

$$\lambda_2 = \lambda_1 + \Delta\lambda$$

$$\Delta\lambda \approx \frac{\lambda_1^2}{8nd\cos(\theta_2)}$$

wherein n represents a refractive index, d represents average thickness of the transparent substrate, and θ2 represents a refraction angle.

6. A thickness measuring apparatus comprising:
a first laser configured to output a first laser beam of a first wavelength;
a second laser configured to output a second laser beam of a second wavelength;
an optical coupler configured to couple an output of the first laser and an output of the second laser with each other and to transmit a combined output through a first position of a transparent substrate;
a dichromatic beam splitter configured to split a first transmitted beam of the first wavelength and a second transmitted beam of the second wavelength from each other;
a first optical detector configured to measure the first transmitted beam of the first wavelength split through the dichromatic beam splitter;
a second optical detector configured to measure the second transmitted beam of the second wavelength split through the dichromatic beam splitter; and
a processing unit configured to extract a rotation angle on a Lissajous graph using one of:
  an intensity of the first transmitted beam of the first wavelength and an intensity of the second transmitted beam of the second wavelength,
  a difference in optical path length between adjacent rays caused by internal reflection of the transparent substrate at the first position, and
  a phase difference between adjacent rays caused by the internal reflection of the transparent substrate at the first position,
wherein the processing unit comprises:
  an A-D converter configured to convert a first measurement signal of the first laser beam and a second measurement signal of the second laser beam to digital signals;
  a nonlinear correction unit configured to perform nonlinear correction using digitally converted first and second measurement signals;
  a check point confirm unit configured to confirm whether a phase difference corresponding to the rotation angle calculated during each phase calculation becomes integer multiple of π/4;
  a parameter update unit configured to update a parameter when the phase difference corresponding to the rotation angle is integer multiple of π/4; and
  a phase calculator configured to calculate the phase difference corresponding to the rotation angle.

7. The thickness measuring apparatus of claim 6, wherein the intensity of the first transmitted beam of the first wavelength has a cosine function according to the phase difference, and the intensity of the second transmitted beam of the second wavelength has a sine function according to the phase difference.

8. The thickness measuring apparatus of claim 6, wherein the optical coupler comprises:
a beam splitter configured to transmit the first laser beam of the first wavelength and to reflect the second laser beam of the second wavelength; and
a reflection mirror configured to reflect the second laser beam of the second wavelength to the beam splitter.

9. The thickness measuring apparatus of claim 6, further comprising:
a transfer unit configured to position the transparent substrate; and
a transfer driving unit configured to drive the transfer unit.

10. A thickness measuring apparatus comprising:
a first laser configured to output a first pulse beam having a first wavelength and a first period;
a second laser configured to output a second pulse beam oscillating at a different time from the first pulse beam and having a second wavelength and the first period;
an optical coupler configured to provide an output of the first laser or an output of the second laser to a first position of a transparent substrate;
an optical detector sequentially measuring a first transmitted pulse beam of the first wavelength and a second transmitted pulse beam of the second wavelength transmitted through the transparent substrate; and
a processing unit configured to extract a rotation angle on a Lissajous graph using one of:
  an intensity of the first transmitted pulse beam of the first wavelength and an intensity of the second transmitted pulse beam of the second wavelength,
  a difference in optical path length between adjacent rays caused by internal reflection of the transparent substrate at the first position, and
  a phase difference between adjacent rays caused by the internal reflection of the transparent substrate at the first position,
wherein the processing unit comprises:
  an A-D converter configured to convert a first measurement signal of the first pulse beam and a second measurement signal of the second pulse beam to digital signals;
  a nonlinear correction unit configured to perform nonlinear correction using digitally converted first and second measurement signals;
  a check point confirm unit configured to confirm whether a phase difference corresponding to the rotation angle calculated during each phase calculation becomes integer multiple of π/4;
  a parameter update unit configured to update a parameter when the phase difference corresponding to the rotation angle is integer multiple of π/4; and
  a phase calculator configured to calculate the phase difference corresponding to the rotation angle.

11. The thickness measuring apparatus of claim 10, wherein the intensity of the first transmitted pulse beam of the first wavelength has a cosine function according to the phase difference, and the intensity of the second transmitted pulse beam of the second wavelength has a sine function according to the phase difference.

12. The thickness measuring apparatus of claim 10, wherein the optical coupler comprises:
   a beam splitter configured to transmit the first pulse beam and to reflect the second pulse beam; and
   a reflection mirror configured to reflect the second pulse beam to the beam splitter.

13. The thickness measuring apparatus of claim 10, further comprising:
   a transfer unit configured to position the transparent substrate; and
   a transfer driving unit configured to drive the transfer unit.

14. A thickness measuring apparatus comprising:
   a first laser configured to output a first laser beam of a first wavelength;
   a second laser configured to output a second laser beam of a second wavelength;
   an optical switch configured to receive an output of the first laser and an output of the second laser and to periodically and alternately provide the first laser beam and the second laser beam to a first position of a transparent substrate;
   an optical detector configured to measure a first transmitted beam of the first wavelength or a second transmitted beam of the second wavelength transmitted through the transparent substrate; and
   a processing unit extracting a rotation angle on a Lissajous graph using one of:
      an intensity of the first transmitted beam of the first wavelength and an intensity of the second transmitted beam of the second wavelength,
      a difference in optical path length between adjacent rays caused by internal reflection of the transparent substrate at the first position, and
      a phase difference between adjacent rays caused by the internal reflection of the transparent substrate at the first position,
   wherein the processing unit comprises:
      an A-D converter configured to convert a first measurement signal of the first laser beam and a second measurement signal of the second laser beam to digital signals;
      a nonlinear correction unit configured to perform nonlinear correction using digitally converted first and second measurement signals;
      a check point confirm unit configured to confirm whether a phase difference corresponding to the rotation angle calculated during each phase calculation becomes integer multiple of $\pi/4$;
      a parameter update unit configured to update a parameter when the phase difference corresponding to the rotation angle is integer multiple of $\pi/4$; and
      a phase calculator configured to calculate the phase difference corresponding to the rotation angle.

15. The thickness measuring apparatus of claim 14, wherein the intensity of the first transmitted beam of the first wavelength has a cosine function according to the phase difference, and the intensity of the second transmitted beam of the second wavelength has a sine function according to the phase difference.

16. The thickness measuring apparatus of claim 14, further comprising:
   a transfer unit configured to position the transparent substrate; and
   a transfer driving unit configured to drive the transfer unit.

17. A thickness measuring apparatus comprising:
   a first laser configured to output a first laser beam of a first wavelength;
   a second laser configured to output a second laser beam of a second wavelength;
   a wavelength-division multiplexer configured to receive and multiplex the first laser beam and the second laser beam into a single output and to provide the single output to a first position of a transparent substrate;
   an optical detector configured to measure a first transmitted beam of the first wavelength or a second transmitted beam of the second wavelength transmitted through the transparent substrate; and
   a processing unit extracting a rotation angle on a Lissajous graph using one of:
      an intensity of the first transmitted beam of the first wavelength and an intensity of the second transmitted beam of the second wavelength,
      a difference in optical path length between adjacent rays caused by internal reflection of the transparent substrate at the first position, and
      a phase difference between adjacent rays caused by the internal reflection of the transparent substrate at the first position,
   wherein the processing unit comprises:
      an A-D converter configured to convert a first measurement signal of the first laser beam and a second measurement signal of the second laser beam to digital signals;
      a nonlinear correction unit configured to perform nonlinear correction using digitally converted first and second measurement signals;
      a check point confirm unit configured to confirm whether a phase difference corresponding to the rotation angle calculated during each phase calculation becomes integer multiple of $\pi/4$;
      a parameter update unit configured to update a parameter when the phase difference corresponding to the rotation angle is integer multiple of $\pi/4$; and
      a phase calculator configured to calculate the phase difference corresponding to the rotation angle.

18. The thickness measuring apparatus of claim 17, further comprising:
   a wavelength-division demultiplexer configured to receive the first transmitted beam and the second transmitted beam through a single input port, to output the first transmitted beam to a first output port, and to output the second transmitted beam to a second output port,
   wherein the optical detector comprises:
      a first optical detector connected to the first output port of the wavelength-division demultiplexer; and
      a second optical detector connected to the second output port of the wavelength-division demultiplexer.

19. The thickness measuring apparatus of claim 17, wherein the first laser beam and the second laser beam are in form of a periodical pulse, and
   wherein the first laser beam and the second laser beam do not temporally overlap each other.

20. A thickness measuring apparatus comprising:
   a first laser configured to output a first laser beam of a first wavelength;
   a second laser configured to output a second laser beam of a second wavelength;
   an optical coupler configured to receive and output the first laser beam and the second beam to a single path;

a pattern beam generator disposed between the optical coupler and a transparent substrate and configured to generate a pattern beam;

an optical detector array configured to measure a first transmitted beam of the first wavelength and a second transmitted beam of the second wavelength transmitted through the transparent substrate; and a processing unit extracting a rotation angle on a Lissajous graph using one of:
  an intensity of the first transmitted beam of the first wavelength and an intensity of the second transmitted beam of the second wavelength,
  a difference in optical path length between adjacent rays caused by internal reflection of the transparent substrate at the first position, and
  a phase difference between adjacent rays caused by the internal reflection of the transparent substrate at the first position, wherein the processing unit comprises:
  an A-D converter configured to convert a first measurement signal of the first laser beam and a second measurement signal of the second laser beam to digital signals;
  a nonlinear correction unit configured to perform nonlinear correction using digitally converted first and second measurement signals;
  a check point confirm unit configured to confirm whether a phase difference corresponding to the rotation angle calculated during each phase calculation becomes integer multiple of $\pi/4$;
  a parameter update unit configured to update a parameter when the phase difference corresponding to the rotation angle is integer multiple of $\pi/4$; and
  a phase calculator configured to calculate the phase difference corresponding to the rotation angle.

21. The thickness measuring apparatus of claim 20, wherein the pattern beam generator comprises:
  a diffraction grating element configured to diffract a received beam to generate a plurality of beams aligned in a constant direction; and
  a collimation lens configured to convert the plurality of beams into parallel rays.

* * * * *